US008973747B2

(12) United States Patent
Schlottig et al.

(10) Patent No.: US 8,973,747 B2
(45) Date of Patent: Mar. 10, 2015

(54) PACKAGE FOR DENTAL IMPLANT

(75) Inventors: Falko Schlottig, Füllinsdorf (CH); Uwe Werner, Uitikon Waldegg (CH); Daniel Irányi, Steinhausen (CH); Matthias Günthart, Aarau (CH); Nico Spinelli, Zürich (CH)

(73) Assignee: Thommen Medical AG, Waldenburg (CH)

( * ) Notice: Subject to any disclaimer, the term of this patent is extended or adjusted under 35 U.S.C. 154(b) by 979 days.

(21) Appl. No.: 12/990,938

(22) PCT Filed: Jun. 3, 2009

(86) PCT No.: PCT/EP2009/056790
§ 371 (c)(1),
(2), (4) Date: Nov. 3, 2010

(87) PCT Pub. No.: WO2009/147166
PCT Pub. Date: Dec. 10, 2009

(65) Prior Publication Data
US 2011/0056851 A1    Mar. 10, 2011

(30) Foreign Application Priority Data

Jun. 6, 2008 (CH) ................................. 0861/08

(51) Int. Cl.
*A61B 19/02* (2006.01)
*A61C 8/00* (2006.01)

(52) U.S. Cl.
CPC .................................. *A61C 8/0087* (2013.01)
USPC .......................................... 206/63.5; 206/368

(58) Field of Classification Search
USPC ........ 206/368, 63.5, 493, 369, 438, 363, 205, 206/206, 207
See application file for complete search history.

(56) References Cited

U.S. PATENT DOCUMENTS

| 5,368,160 A | 11/1994 | Leuschen et al. |
| 6,083,229 A * | 7/2000 | Constantz et al. .............. 606/92 |

(Continued)

FOREIGN PATENT DOCUMENTS

| EP | 1 523 955 A1 | 4/2005 |
| EP | 1 749 501 A1 | 2/2007 |

(Continued)

*Primary Examiner* — Jacob K Ackun
*Assistant Examiner* — Jenine Pagan
(74) *Attorney, Agent, or Firm* — Sughrue Mion, PLLC

(57) ABSTRACT

Package (1) for an implant (2), in particular for a dental implant, comprising a housing (5) with a compartment (51) that can be closed by way of a pivotable and/or slidable cover (4) so as to be essentially liquid-tight, said compartment being intended for a first section (2') of the implant (2), and an area (19) for a second section (3) of the implant (2), said area being separated rated from the compartment (51) by way of a housing wall (8), wherein a passage (35) connecting the compartment (51) and said area (19) is provided in the housing wall (8) for a transition section (3') between the first section (2') and the second section (3) of the implant (2), and wherein the housing wall (8) comprises a removal slot (9, 36) for removal of the implant when the cover (4) is open without separating the sections (2, 3). The package (1) comprises at least one fluid cartridge (12) and an associated release element (18) and the fluid cartridge (12) can be opened by way of the release element (18) when the cover (4) is closed such that fluid located in the fluid cartridge (12) can flow out into the compartment (51).

15 Claims, 12 Drawing Sheets

(56) References Cited

U.S. PATENT DOCUMENTS

| | | | |
|---|---|---|---|
| 6,149,655 A * | 11/2000 | Constantz et al. | 606/94 |
| 7,694,812 B2 * | 4/2010 | Bammerlin et al. | 206/368 |
| 2004/0045999 A1 * | 3/2004 | Babij, Jr. | 227/119 |
| 2007/0068827 A1 * | 3/2007 | Jemelin | 206/63.5 |
| 2007/0072148 A1 | 3/2007 | Memmolo et al. | |
| 2007/0074980 A1 * | 4/2007 | Bankoski et al. | 206/219 |
| 2007/0181446 A1 | 8/2007 | Donahoe et al. | |
| 2007/0193905 A1 * | 8/2007 | Jemelin et al. | 206/438 |
| 2007/0295620 A1 | 12/2007 | Collet et al. | |

FOREIGN PATENT DOCUMENTS

| | | |
|---|---|---|
| WO | 99/65416 A1 | 12/1999 |
| WO | 2005/037126 A1 | 4/2005 |
| WO | 2006/031162 A1 | 3/2006 |
| WO | 2008/047976 A1 | 4/2008 |

\* cited by examiner

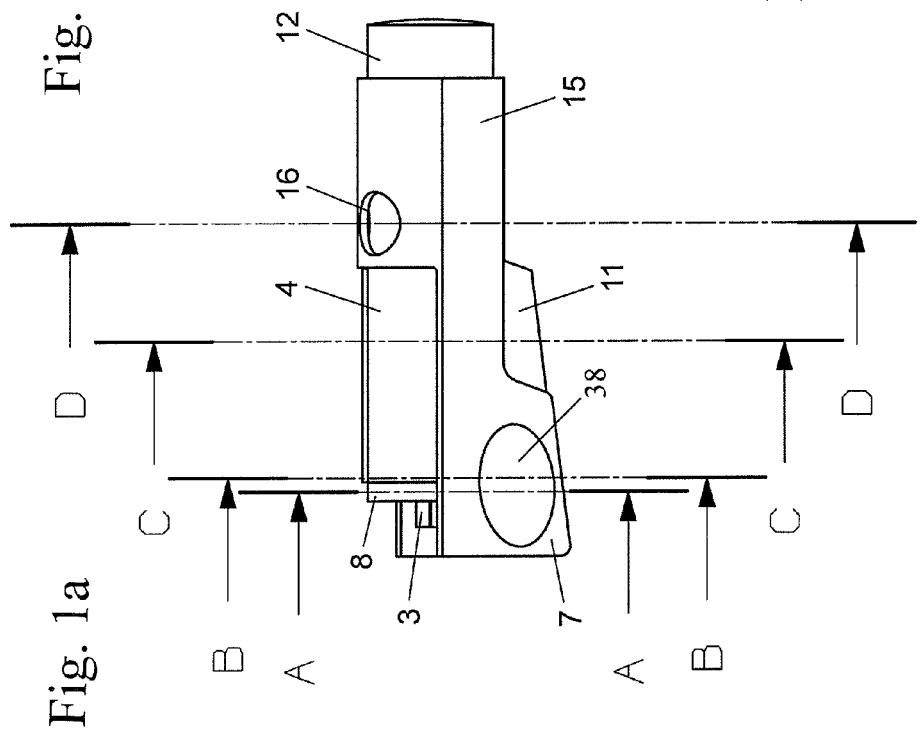

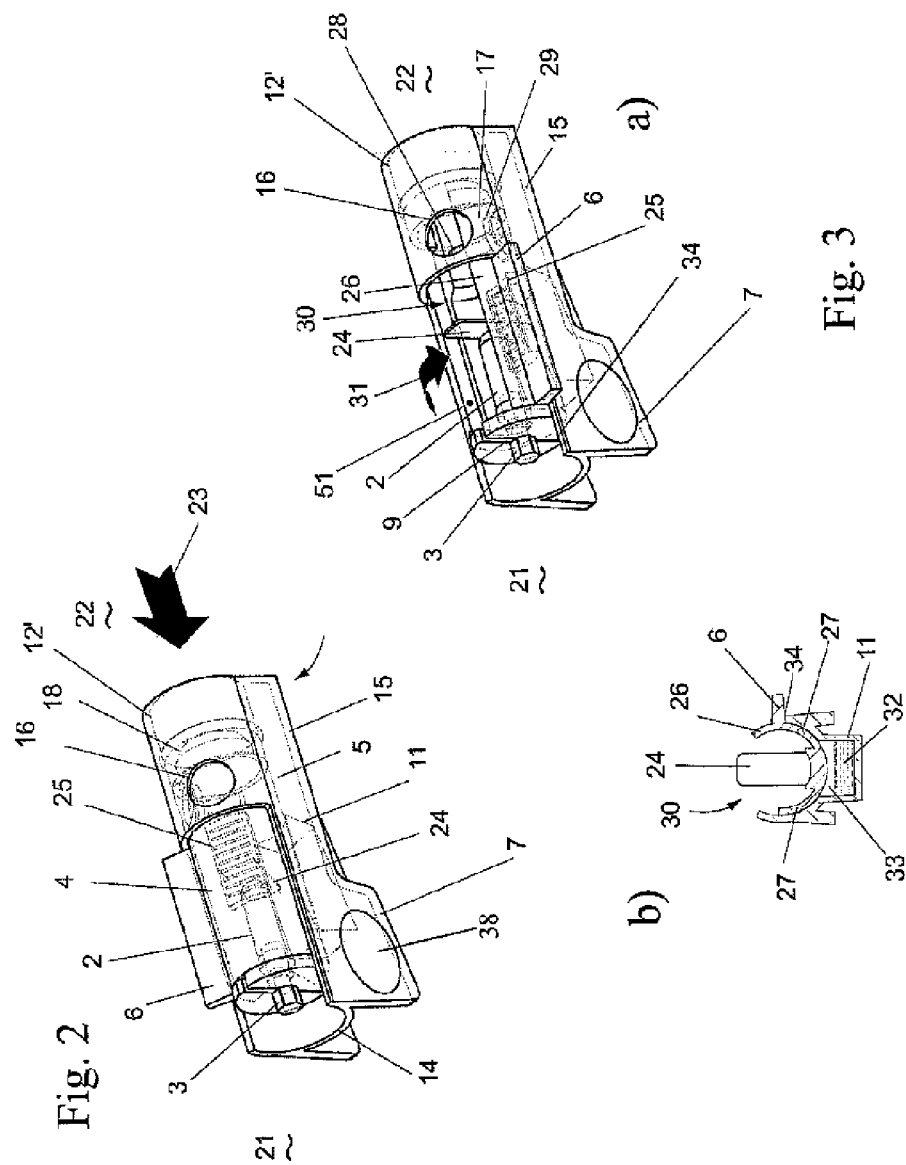

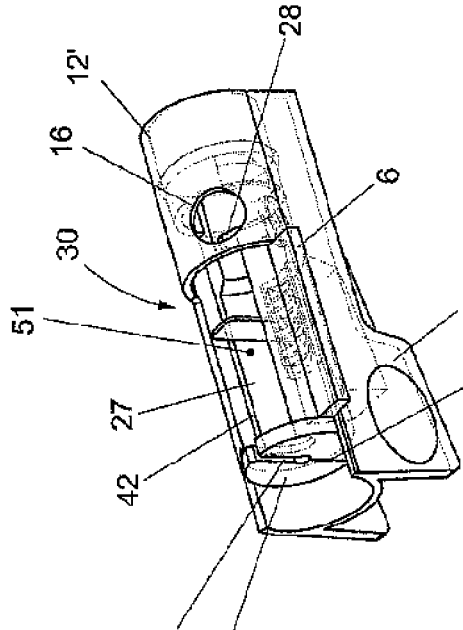
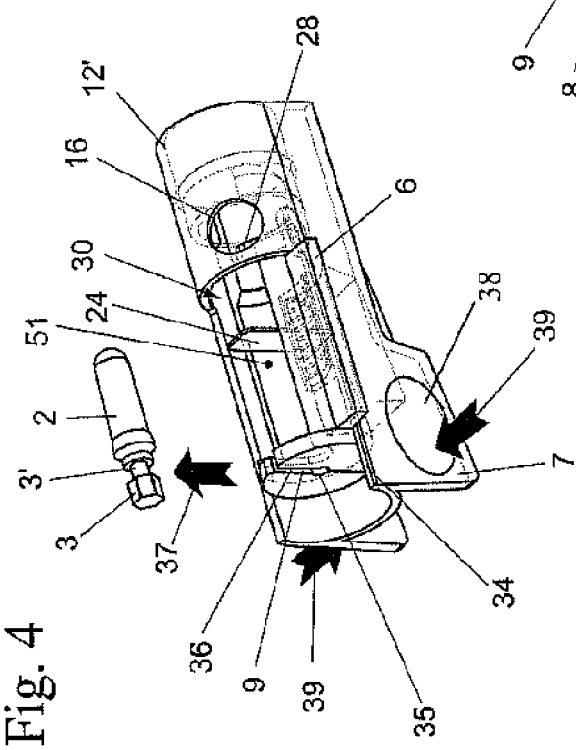

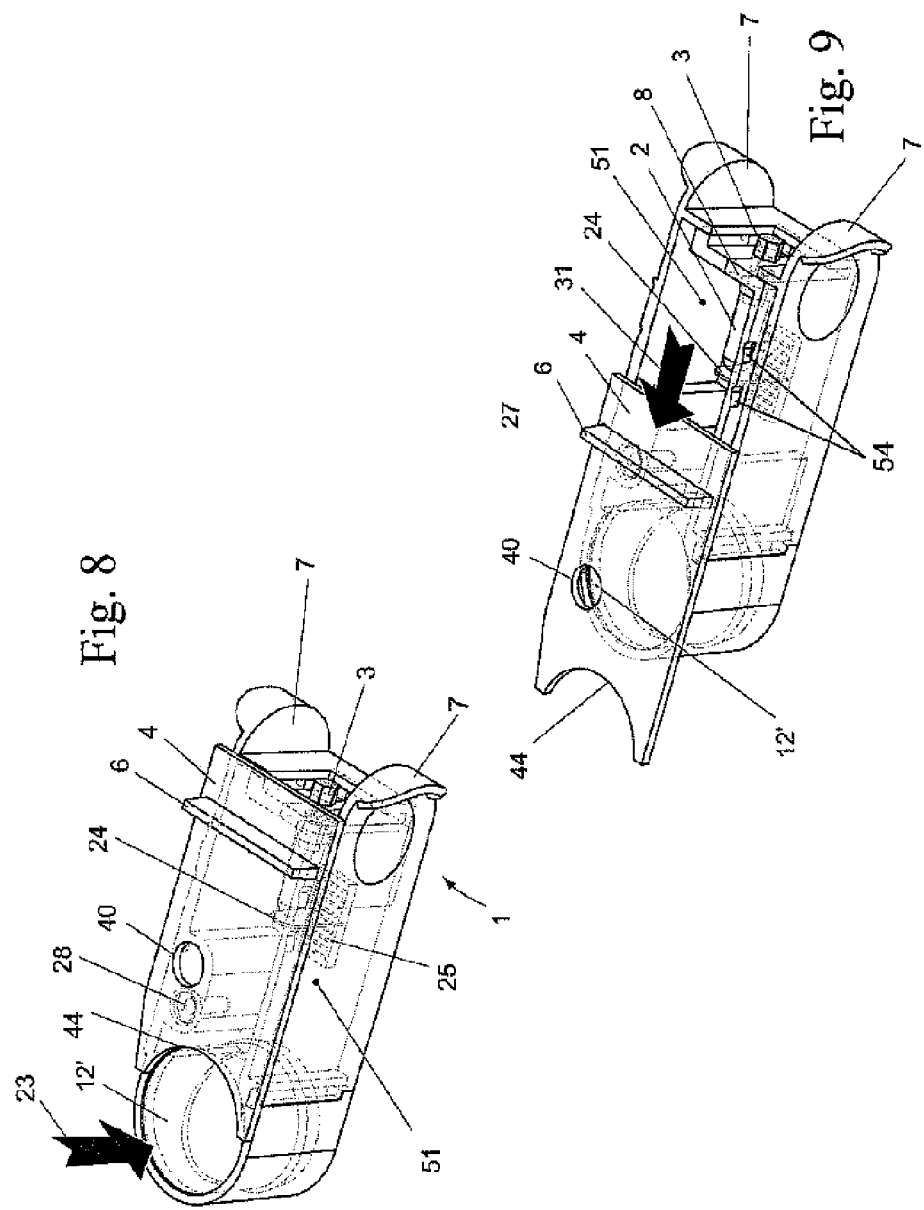

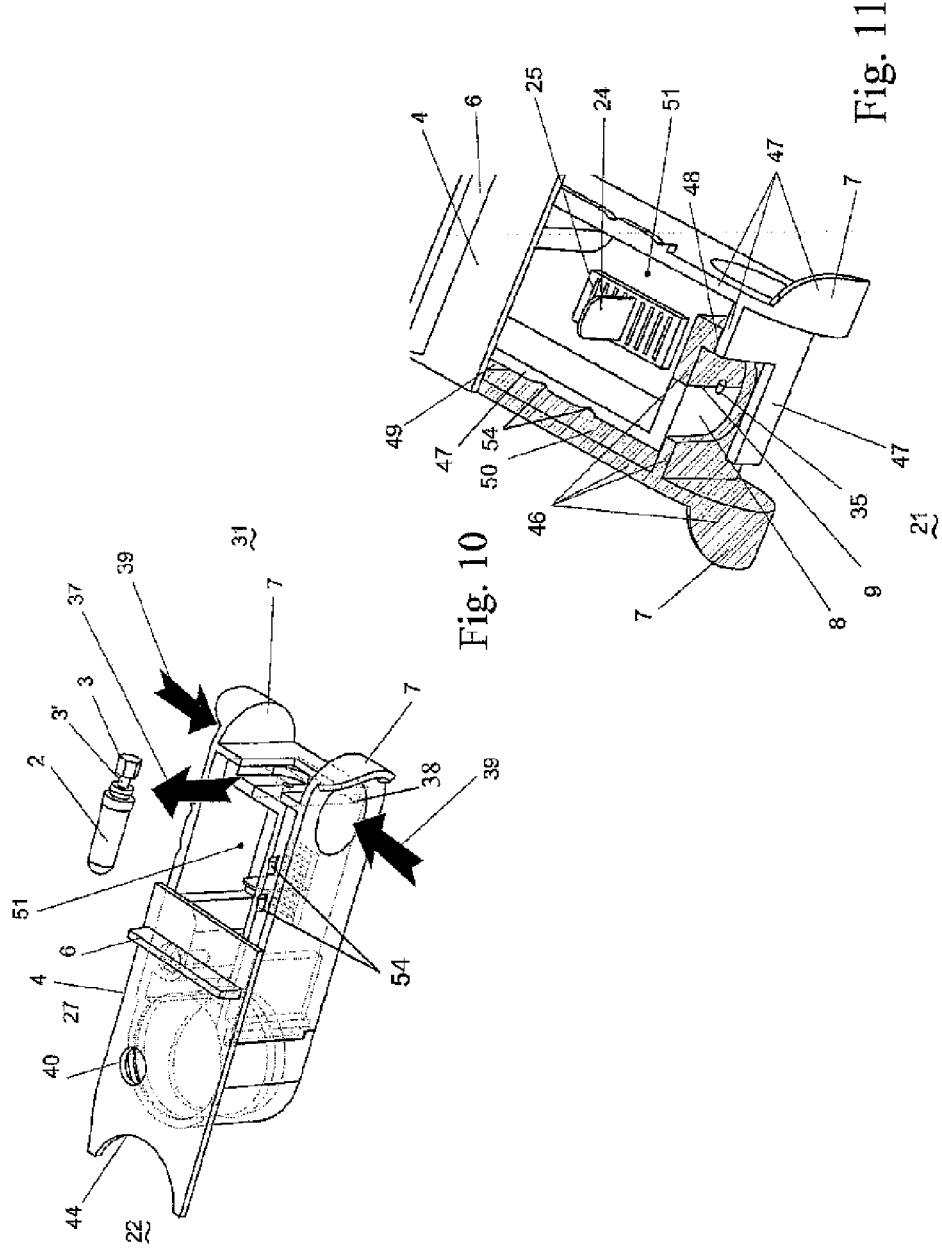

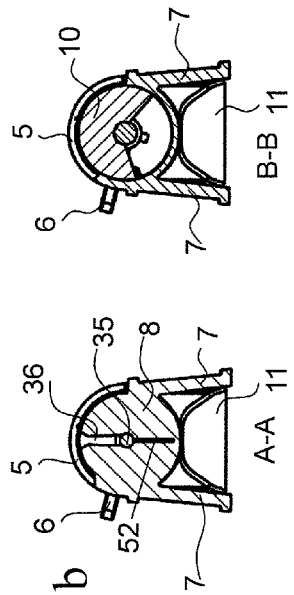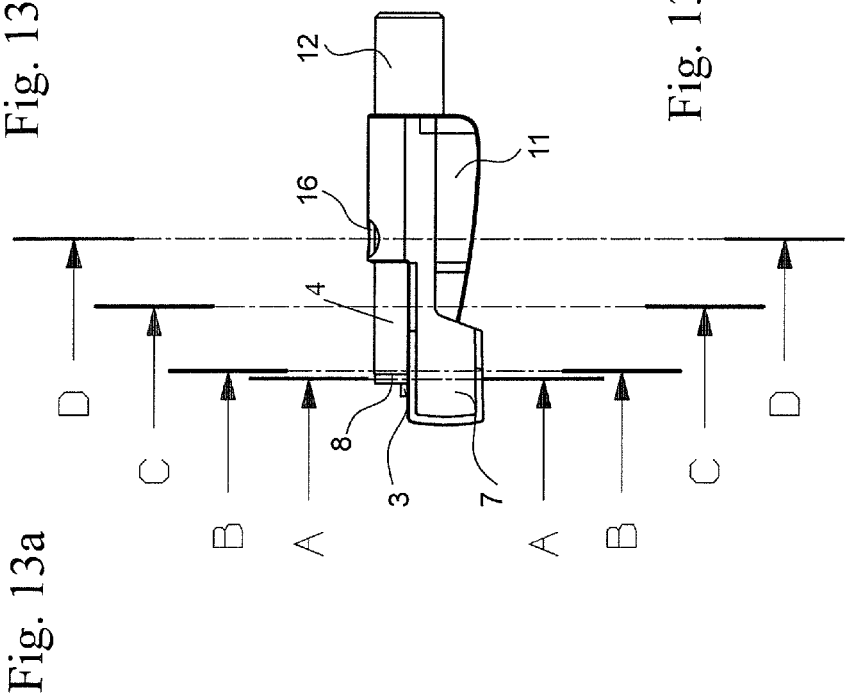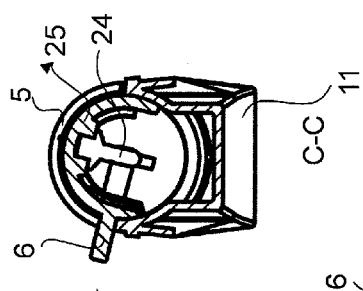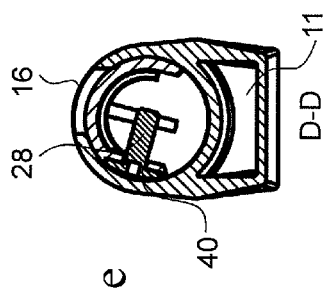

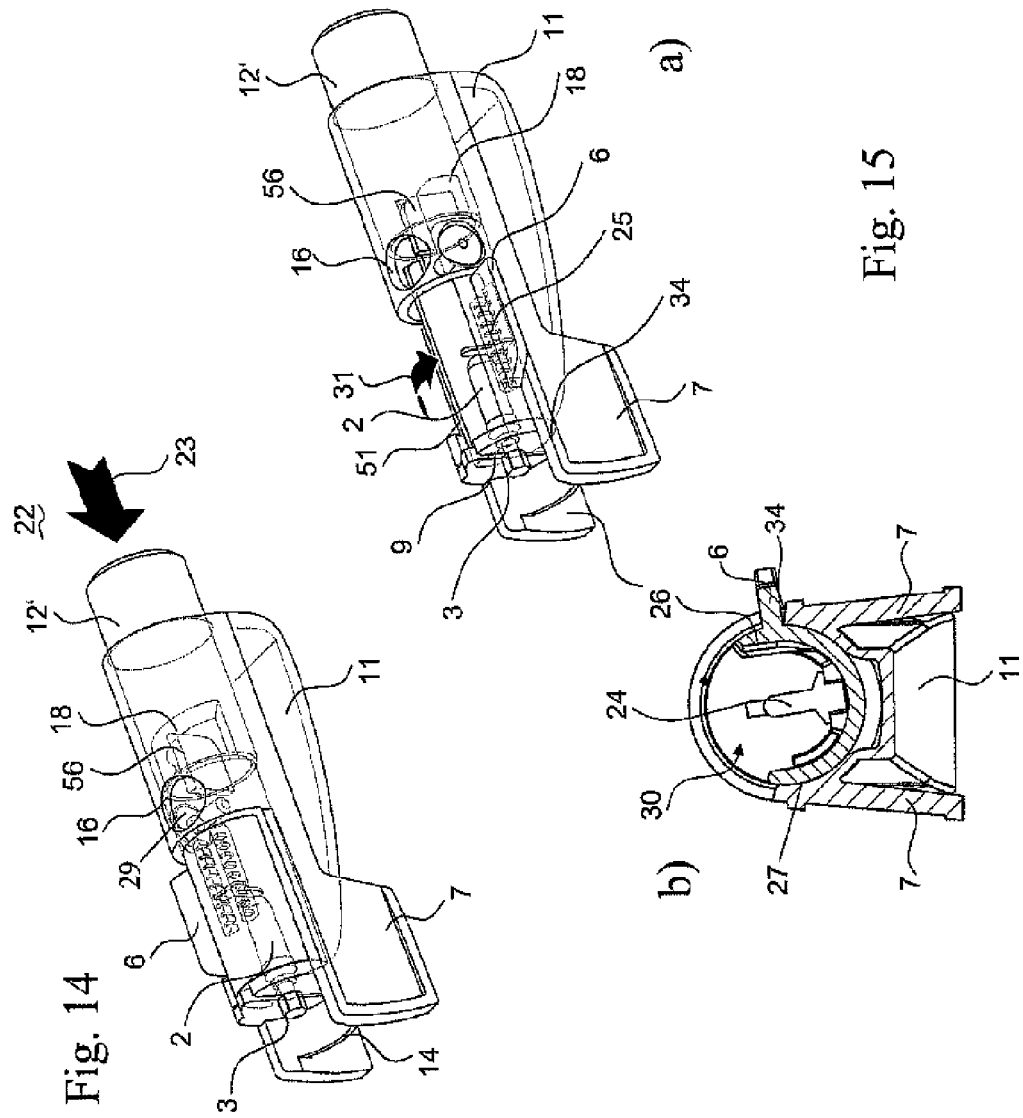

PACKAGE FOR DENTAL IMPLANT

TECHNICAL FIELD

The present invention relates to a package for an implant, in particular a dental implant, and to a method for preparing an implant, in particular a dental implant, for insertion into the human body or into human tissue.

PRIOR ART

It is known, in particular from the field of dental implants, that is to say the implants that are made for example of ceramic or a special metal material in the form of a pin with an external thread, to design special sterile packages which on the one hand allow troublefree transportation of the dental implants and on the other hand allow handling that is as easy and reliable as possible during the corresponding operation. Furthermore, such packages are intended to allow the type or size of implant in the container to be ascertained, normally from the outside, without the packages already having been opened.

For example, U.S. Pat. No. 5,368,160 describes a specific cylindrical container for such an implant in which the healing cap is arranged in the cover of the actual container.

EP 1 749 501 likewise describes a substantially rotationally symmetrical package for dental implants, but the application mainly concerns a holding element for such an implant, that is to say an element to which the implant is fastened and which allows the implant to be connected as easily as possible to a tool for the subsequent insertion of the implant into the human body.

A package for dental implants is likewise described by WO 99/65416; here, too, the package is of a substantially cylindrical form and there is a pivotable cover which, when opened, exposes the healing cap on its inner side and exposes the mounting arrangement on the dental implant on the other side.

This is so because such dental implants are not made available to dentists simply as the actual implants alone but rather are always supplied from the outset as a unit with a mounting arrangement, which is let into an inner recess or outer connecting means of the implant. This allows the implant to be connected to the corresponding tool (for example torque wrench or the like) directly at this mounting arrangement, without the implant having to be taken up by hand or in a tool each time.

A package for a dental implant of this type is likewise described by US 2007/0181446; here, too, the package is substantially cylindrical and is specifically designed for receiving different sizes of dental implants in a favorable and troublefree manner.

A further multi-part package for such an implant is described in WO 2008/047976.

It is also known that wetting of a dental implant, preferably just before its insertion into the human body, may be of advantage. Correspondingly, the conventional procedure is that the implant is removed from the package out of a container, such as that represented for example in the aforementioned documents, while being correspondingly held by the mounting holder, and is then immersed in an immersion bath in a separate container. This requires a large number of error-prone manipulations, which is undesired.

SUMMARY OF THE INVENTION

The invention is accordingly based on the object of providing an improved package for implants.

This object is achieved by proposing a package for an implant, in particular for a dental implant, with a housing, which has a compartment for a first portion of the implant (the actual implant) that can be closed by a pivotable and/or slidable cover so as to be substantially liquid-tight. The term "liquid-tight" in connection with this compartment should be understood as meaning a liquid tightness suitable for the intended use. In particular, this means that the compartment is sufficiently liquid-tight to allow, for example, shaking of the package as a whole at the moment when the liquid is released from the liquid cartridge and the liquid flows into the compartment, largely without the liquid escaping. Typically sufficient is a liquid tightness such that no more than a few drops can escape during normal shaking to wet the implant. Really complete liquid tightness, however, is preferably not required, since after all the liquid is stored in the liquid cartridge and only has to be kept in this compartment for the wetting just before implantation. In this connection, the implant is particularly the unit comprising the actual implant and a mounting holder such as that typically provided at or in the implant for the mounting of the same. In the actual compartment, only the actual implant, that is to say the part that is later inserted in the human body or in the human bone/tissue, is arranged (as well as the part of the mounting holder fastened therein). The package also has a region for a second portion of the implant that is separated from the compartment by a housing wall (indeed typically the mounting portion mentioned, or the region thereof on which a tool can act), wherein a passage connecting the compartment and this region is present in the housing wall for a transitional portion between the first portion and the second portion of the implant. In other words, the second portion, that is to say the front part of the mounting arrangement in the specific case mentioned above, protrudes out and is not arranged in the compartment. In order that, when a tool is preferably fastened to the mounting holder, the implant can be removed from the package without the actual implant and the mounting holder being separated, the package, or specfically the housing wall, has a removal slot, which allows the implant to be removed when the cover is open, without separating the portions. This removal slot is typically of an upwardly open form. Furthermore, the package has, according to the invention, at least one liquid cartridge and an associated release element, wherein a liquid with which the implant can be wetted, rinsed, conditioned, chemically or biochemically or pharmaceutically modified or coated on the surface or else within the implant (for example in the case of a porous or sponge-like surface) as preparation before it is inserted into the human body is normally arranged in this liquid cartridge. Therefore, with the cover closed, the liquid cartridge can normally be opened by means of the release element in such a way that liquid located in the liquid cartridge can flow out into the compartment with the cover closed in the normal way. The liquid cartridge does not in this case necessarily have to be already arranged in the package, but rather it is also possible to provide such a package just with a receptacle for a liquid cartridge, and to fit the liquid cartridge, which can for example be produced separately and in a sterile manner and which may, for example, also contain different liquids adapted to the requirements, into or onto such a housing. Thus, for example, packages with implants of different sizes and liquid cartridges with liquids for different surface treatments can be separately provided (kit of parts), in order to increase the flexibility both in production and in practical use. Such combination packages or kit of part arrangements are also covered by the present invention.

One of the key points of the present invention is therefore to provide a package for an implant that is provided directly with a container with liquid, and this container or the liquid present in it is arranged separately from the implant and, correspondingly, the liquid does not initially come into contact with the implant. It therefore concerns a package in which a liquid is only intended to be brought into contact with the implant during preparation for removal.

However, it is also possible that there is already a liquid in the compartment and the liquid in the liquid cartridge can be admixed with this liquid already present in the compartment just before the removal of the implant. This is of advantage, for example, whenever the combined liquids are not stable (for example flocculation or the like), or if the implant is generally intended to be stored in a first liquid, and a second liquid or a second component is only intended to be brought into contact with the implant just before removal. A further key point is, furthermore, to design such a package specifically in such a way that the implant or the part to be removed is not arranged completely in the package but at least partially protrudes into open space from the region in which the wetting by the liquid is intended to take place. In particular whenever the part be removed has, for example, a mounting region, mounting attachment or a mounting holder, which are in any case only provided for holding on a tool or for subsequent fastening of a further part (for example a crown), it is indeed not necessary that this part is wetted; it is, rather more, often disadvantageous, because the wetting has the effect, for example, that this region can be taken up less well by the tool. The exposing of this second part or second portion also allows, for example, the package to be fastened on a tool by means of the mounting holder even before the opening of the liquid cartridge, and for example the shaking or vibrating of the package as a whole for the wetting of the implant to be brought about after the opening of the liquid cartridge by the tool. Both the cover and the housing are in this case normally made of rigid plastic.

According to a first preferred embodiment, the housing is formed in an elongated manner with a front end and a rear end, and the region (for the mounting holder or the like) is arranged at the front end, the liquid cartridge is arranged at the opposite rear end or else on the elongated package (preferably at the rear end), and the compartment is arranged in between or thereunder.

Normally, the region is freely accessible with the cover closed, and is provided particularly preferably for a mounting holder for the implant, and this region is preferably exposed in such a way that the mounting holder can be readily taken up by the intended tool and fastened thereto.

According to a further preferred embodiment, the package is characterized in that it is intended for additionally receiving a healing cap.

In this connection, the cover preferably has an opening for the removal of the healing cap and the housing has a housing opening for the removal of the healing cap. There is then no need for a separate cover to be provided for the healing cap if, for example, preferably with the healing cap arranged in the housing (and not in the cover), the housing opening is covered by the cover both when the cover is completely closed and when the cover is completely open and is only exposed in the case of an intermediate position or a position of the cover beyond the opening, by bringing the opening into line with the housing opening. Or if, preferably with the healing cap arranged in or on the cover, the opening is covered by the housing both when the cover is completely closed and when the cover is completely open and is only exposed in the case of an intermediate position of the cover by bringing the opening into line with the housing opening.

A further preferred embodiment is characterized in that the compartment has in the lower region a collecting container for the liquid of the liquid cartridge, which container preferably has a volume which corresponds substantially to the liquid volume of the liquid cartridge or is smaller. In particular with regard to intermediate storage for the time during which the implant is being inserted and the healing cap is not yet intended to be used, it is of advantage if this compartment is closed or at least covered by the cover when the package is completely open. For example by the cover being pushed over the collecting container during opening. The collecting container may in this case be substantially arranged only under the compartment for the implant, but it may also be of an elongated form and extend for example up to the rear end of the package, where the liquid cartridge is arranged. It may serve thereby in this rear region of the package as a standing area for the package. The collecting container may in this case have a bottom sloping downwardly at an angle to the rear, so that liquid collected in it flows to the region at the rear end of the package, where the collecting container is covered from above by further walls of the package.

A first particularly preferred embodiment of the package is distinguished by a substantially cylindrical outer form. Specifically, it is preferably characterized in that the housing has a region in the form of a segment of a hollow cylinder, which together with a cover that is likewise in the form of a segment of a hollow cylinder and arranged coaxially in relation to the region in the form of a segment of a hollow cylinder substantially delimits the compartment (in an axial region of the package). The cover may in this case have an inside diameter which corresponds substantially to the outside diameter of the corresponding housing portion (cover runs over the housing) or it may have an outside diameter which corresponds substantially to the inside diameter of the corresponding housing portion (cover runs to a certain extent in the housing). The cover and the housing portion together form a more or less cylindrical region of the package; the cover correspondingly passes over at least the circumference of the housing portion missing from the full circumference or is preferably formed over a relatively great circumferential region, so that, in the closed state, the cover overlaps the housing region either from the outside or from the inside. In this case, the region (in which for example the mounting holder of the implant lies) is preferably separated from the compartment by a housing wall arranged perpendicularly in relation to the axis and preferably in the form of a circular disk or in the form of a segment of a circle (for example also as a lying segment of a circle). This housing wall preferably has a passage (through which the transitional portion of the implant reaches when it is arranged in the package) that is arranged substantially on the axis and is upwardly open by means of a slot, which is preferably narrowed in comparison with the passage. The cover is in this case preferably mounted rotatably about the common axis in the housing, wherein it slides substantially flush on the inner side of the housing, as already explained above, for example with its outer surface (seals which can be fastened to the housing and/or to the cover may optionally be arranged in between in order to be able to ensure the liquid tightness mentioned). The cover can thus be pivoted from a closed state of the package (liquid-tight in the sense of the above definition, typically the actual implant stored in a substantially sterile manner) into an open state (implant can be removed). In order to ensure that sealing is also ensured with respect to the housing wall, the cover may have on its axial periphery, facing the housing wall, a sealing wall portion preferably passing over the same angular range as the cylinder segment of the cover and arranged perpendicularly in relation to the axis.

In order to ensure increased seal-tightness of the space inside the housing for the shaking process, it is possible to provide sealing means on the inner side of the housing wall and/or also in the peripheral regions of the cover on the outer side thereof, where it is adjacent to the housing in the closed state. Alternatively or in addition, it is also possible not to provide the sealing means on the cover but at points on the housing.

In the case of the housing wall, it is possible for example to fasten such a sealing means on the inner side, in the case of a housing wall in the form of a circular disk, as for example in the case of the first and third embodiments presented below, in the form of a circular disk of a flexible sealing film, for example in the form of a polyethylene film (for example LDPE) with a thickness in the range of 0.05-0.5 mm. Further possible materials are polypropylene, polycarbonate, COC, polyamide or else composite films of these materials, for example composite films of polyethylene and polyamide, etc. The sealing film may consist of the same material as the housing at the point of fastening, but it may also consist of a different material. When the sealing film is on the inner side of the housing wall, the upwardly open slot for the removal of the implant may be formed as a single cut in the film, so that there forms there to a certain extent a lip seal, which however nevertheless makes insertion and removal of the implant possible. Otherwise, the sealing film covers the housing wall on the inner side to a certain extent such that it covers over completely the entire surface area of the housing wall. If, to facilitate the removal of the implant, in the housing wall there is, for example, a further slot, which is spread for the removal, this slot is completely covered over by the sealing film, which is unproblematic since the sealing film has sufficient flexibility to make the spreading for removal nevertheless possible.

The sealing film attached to the cover or to the housing in the adjacent region in the closed state may be formed as a strip, for example with a width in the range of 0.1-3 mm.

The sealing films, both on the cover and/or on the housing or on the housing wall may be fastened by various methods, for example using adhesives, crimping, ultrasonic welding, etc.

It is possible in connection with such a package that the region of the elongated housing in the form of a segment of a hollow cylinder protrudes in the axial direction toward a front end beyond the housing wall, at least as far as the second portion of the implant, preferably somewhat further than the latter, and as a result the region that is preferably open in the axial and upward directions is formed. A region for the mounting holder that is indeed open but is closed off in the downward direction in the form of a trough is, to a certain extent, provided in this way. At the opposite rear end, the housing may have a substantially closed region in the form of a hollow cylinder which adjoins the compartment and likewise forms part thereof and in which there is arranged (preferably right at the rear end) a liquid cartridge, which is preferably of a substantially cylindrical form and coaxially arranged and can be pushed in the axial direction into this region, preferably with an exact fit, and/or is rotatable therein. Particularly intuitive handling is possible if, as furthermore preferred, the release element initiates the release of the liquid when the liquid cartridge is pushed into the housing in the axial direction (that is to say toward the compartment), for example as far as a stop, and/or is turned.

This release element, which may be a component part of either the liquid cartridge or the housing or the cover, may generally be a spike, a cutting edge or a projection, which, for example, tears open, pierces or releases a membrane or other predetermined breaking point of the liquid cartridge. Other mechanisms are, however, likewise possible. The membrane may also be perforated by the release element, and/or it may be pierced with needles. According to a preferred embodiment, the release element may in this case be formed as a cutting edge that is inclined with respect to the plane of the membrane, so that, when the release element is displaced into the membrane substantially perpendicularly in relation to the plane of the membrane, the release element cuts successively into the membrane. It is most particularly preferred for the cutting edge to be an inclined cutting edge running around in an at least partly surrounding manner (made to extend on a portion of a circle, for example a semicircle or three-quarter circle). Particularly preferably, the release element may additionally comprise a membrane opening element, which pushes or flips the membrane to the side after it has been opened up by the cutting edge. Thus, together with or after the cutting by the cutting edge or the spike, the membrane is also actually removed from the opening that was closed by the membrane, and so the liquid is effectively released. As a result of the often small dimensions of the opening of the liquid container and the sometimes high surface tension of the liquid held therein, such specific removal of the membrane may be hugely important.

In the case of such a more or less cylindrical package, the region of the housing in the form of a segment of a hollow cylinder may cover an angular range around the axis of 120-210°, preferably in the range of 160-200°. The portion of the cover in the form of a segment of a hollow cylinder may for its part cover an angular range of 120-270°, preferably of 200-250°. A particularly practical and elegant package is obtained if the region of the housing forms approximately the lower half) (180°, and the cover passes over a somewhat larger angular range (for example 200-220°; the region of the housing then forms to a certain extent a lower trough, which also extends still further toward the front end and forms the open region, while the cover only reaches as far as the housing wall.

In particular with regard to easy removal of the implant after its wetting, it is of advantage if the housing has, at least at its front end, two lateral, downwardly protruding feet (standing stability), preferably arranged tangentially and substantially parallel to each other or widening downwardly (inverted V-shaped) (typically of equal length), and preferably webs adjoining thereto and extending toward the rear end (additional stabilization of the standing also in the rear region), wherein the housing wall is joined on in such a way that pressing together of the two feet brings about a widening of the narrowed slot that facilitates the removal of the implant.

A further preferred embodiment of the package is characterized in that the housing is substantially formed as an elongated, upwardly open box, in that the region into which the mounting arrangement normally protrudes out of the package is arranged at a front end and the liquid cartridge is arranged at an opposite rear end. The liquid cartridge may in this case preferably be of a cylindrical form with its axis perpendicular to the longitudinal direction of the housing, that is to say the package may also be designed such that it is rounded off in the rear region. The liquid cartridge may be arranged such that it protrudes at least partially upward out of the package. The cover closes this upper opening and can be displaced along the longitudinal direction of the housing toward the rear end, exposing the upper opening. Alternatively, however, it is also possible to design the cover such that it exposes the opening in a pivoting movement (for example about the axis of the liquid cartridge). This opening displacement of the cover is preferably only possible if the liquid cartridge has either been removed from the housing or has been pressed into the housing, thereby releasing the liquid. This is possible, for example, by the liquid cartridge being pressed to a certain extent completely into the housing and the cover subsequently being able to move over it.

Such a package is preferably characterized in that the housing wall is formed by a first housing part and a second housing part, in that the slot or the widened region and the narrowed or even closed region (completely adjacent to each other) are delimited on one side by the first housing part and on the other side by the second housing part, and in that the first housing part can be displaced in relation to the second housing part substantially in a direction perpendicular to the longitudinal axis of the housing, thereby widening or opening the region. On account of the fact that the two sides of the slot are formed by different parts, the displacement of the two housing parts with respect to each other has the effect that this slot opens, and the implant can be removed upwardly out of the slot much more easily (or only then).

In connection with such a structural design, preferably means are provided, or design measures are taken, preventing the possibility of the slot being opened even when the cover is closed (for example during shaking), and correspondingly the implant being partially released. This may preferably take place by both the first housing part and the second housing part forming at least one lateral wall portion arranged on the same side of the housing, by these two wall portions being spaced apart by a gap, and by the cover having at its end facing the front end a guiding web, which at least partially engages in this gap. If in the case of such a structural design, the cover is in the closed position, the gap is thus filled by this guiding web and the two housing parts cannot be displaced with respect to each other. If the cover is then displaced rearwardly, the guiding web is displaced out of the front region of the gap and, on account of the flexibility of the materials that are normally used, the front region of the gap can then be narrowed and, as a result, the opening can be released (this can also be assisted by a spring element, for example a small spring plate).

Preferably used as materials for the package, including the cover, the housing and the liquid cartridge, are plastics, for example PMMA, PA, for example Grilamid TR (Ems Chemie AG, CH) POM, PET, PBT, polyethylene, polypropylene, fluoropolymers, PEEK, PPS, styrene polymers, polycarbonates, for example Makrolon, and polyimides, COC (cycloolefin copolymer), optionally in combination with a layer of aluminum. The use of these materials, individually or in combination (bicomponent type of construction or, for example, cover of a different material than the housing or the liquid cartridge) is possible and of advantage for all the embodiments described. Materials that are preferably used for the liquid cartridge (also for the membrane) are ones which are water- and vapor-tight, even after sterilizing by gamma rays. It is thus possible, for example, to produce the liquid cartridge from COC (for example from Topas, obtainable from TOPAS Advanced Polymers GmbH, DE) and the rest of the package from polyamide, for example a Grilamid type from the company EMS Chemie, CH.

A film is preferably used as the membrane. A sealing film which can be sealed onto the upper surrounding periphery of the liquid cartridge after the filling thereof, preferably in a hot-sealing process or a cold-sealing process, is preferably used. The film may in this case consist of a single material or else preferably be a composite. The membrane may thus include a layer of aluminum, which has a sealing layer on the side facing the liquid cartridge. The sealing layer may be a polyethylene layer, preferably a layer based on LLDPE. The layer of aluminum may have on the opposite side a further layer of plastic, for example of PET.

In order that the content of the package or the opening of the same can be identified, the cover and/or at least regions of the housing is or are normally of a transparent or translucent form, so that an implant arranged in the package and/or a healing cap arranged in or on the package can be identified.

Furthermore, the present invention relates to a package, such as that which has been described above, with a dental implant arranged in it, wherein a liquid with which the surface of the dental implant is wetted and/or rinsed and/or coated shortly before its insertion into the human body is preferably arranged in the liquid cartridge. This liquid may be, for example, an aqueous solution of a component exhibiting at least one of the following effects (mixtures of such components are also possible): promoting healing, preventing inflammation or infections, promoting bone growth, promoting tissue growth or the attachment of tissue to the implant, preventing bone degradation, stabilizing or improving the bone density in the surroundings of the implant, improving the bone-implant contact by increasing the amount of bone or soft tissue growing on the implant. Possible, for example, are aqueous solutions such as saline solutions, pharmaceutical formulations, and similar systems, as well as mixtures thereof.

Also preferably, such a package is additionally packed in a sterile bag or blister pack. This bag is preferably designed such that it makes manipulation of the package possible when the bag is closed. It may thus consist, for example, of a flexible, at least partially transparent material. It is thus possible that, in a first step, the liquid cartridge is pressed in or turned, with the liquid located therein being released, under non-sterile conditions (for example by assistant personnel) without this bag being opened and the package (including bag) with the dental implant located therein is moved or shaken, wetting said implant. Subsequently, the package prepared in this way (still in the closed bag) is brought into a sterile area and only there is the bag opened. Thus, a further preparational step can be transferred to the prior non-sterile working phase, and so procedures of the process can be improved.

Moreover, the present invention relates to a method for wetting and subsequently removing a dental implant from a package, such as that which has been described above. The method is preferably characterized in that optionally, in a first step, a liquid cartridge with the suitable liquid is inserted into the package or placed on it, in that the liquid cartridge is pressed into the package or turned, with the liquid located therein being released into the compartment, in that the package with the dental implant located therein is moved or shaken, wetting the same, in that the package is opened by displacing or pivoting the cover and the dental implant, taken up by the mounting holder, is removed from the package. Prior to these steps, such a package is normally removed from a sterile bag or blister pack, by the latter being torn open. Optionally, normally after the implant has been inserted, that is to say in an at least indirectly following step, the cover can be partially closed again (or pushed over the opening position) to be precise in such a way that the healing cap is exposed, and the latter is removed from the package.

Further preferred embodiments of the invention are described in the dependent claims.

BRIEF EXPLANATION OF THE FIGURES

The invention is intended to be explained in more detail below on the basis of exemplary embodiments in connection with the drawings, in which:

FIG. 1 shows a perspective view of a closed package according to a first exemplary embodiments;

FIG. 1a) shows a side view of the closed package;

FIG. 1b) shows a section according to A-A perpendicularly to the axis through the front terminating plate;

FIG. 1c) shows a section according to B-B perpendicularly to the axis through the sealing region of the cover;

FIG. 1d) shows a section according to C-C perpendicularly to the axis through the central region of the cover;

FIG. 1e) shows a section according to D-D perpendicularly to the axis through the opening for the healing cap;

FIG. 2 shows a perspective view of a package according to FIG. 1, wherein the liquid cartridge has been pressed in;

FIG. 3 shows a perspective view of an opened package according to FIG. 1 in FIG. 3a) and in FIG. 3b) a section perpendicularly to the axis at the level of the delimiting strip;

FIG. 4 shows a perspective view of an opened package according to FIG. 1, in which the implant is removed;

FIG. 5 shows a perspective view of an opened and empty package according to FIG. 1;

FIG. 8 shows a perspective view of a package according to FIG. 7, wherein the liquid cartridge has been pressed in;

FIG. 9 shows a perspective view of an opened package according to FIG. 7;

FIG. 10 shows a perspective view of an opened package according to FIG. 7, in which the implant is removed;

FIG. 11 shows a perspective view of the front sealing region of an opened and empty package according to FIG. 7;

FIG. 13 shows a perspective view of a closed package according to a third exemplary embodiment;

FIG. 13a) shows a side view;

FIG. 13b) shows a section according to A-A perpendicularly to the axis through the front terminating plate;

FIG. 13c) shows a section according to B-B perpendicularly to the axis through the sealing region of the cover;

FIG. 13d) shows a section according to C-C perpendicularly to the axis through the central region of the cover;

FIG. 13 e) shows a section according to D-D perpendicularly to the axis through the opening for the healing cap;

FIG. 14 shows a perspective view of a package according to FIG. 13, when the liquid cartridge has been pressed in;

FIG. 15 shows a perspective view of an opened package according to FIG. 13a) and in FIG. 13b) a section perpendicularly to the axis at the level of the delimiting strip;

WAYS OF IMPLEMENTING THE INVENTION

Figure 1F:
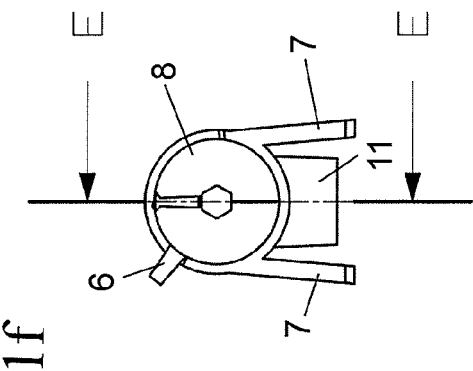
FIG. 1f) shows a frontal view.

The invention is to be explained in more detail below on the basis of exemplary embodiments in connection with the drawings; the drawings and the description which now follows serve for explaining and supporting the actual subject matter for which protection is sought as defined in the claims; the description should not, however, be interpreted in such a way as to restrict the claims.

A first exemplary embodiment of such a package is shown in FIGS. 1 to 6. The package 1 is of a substantially cylindrical form and has a housing 5 and a cover 4, under which the dental implant 2 is arranged. The dental implant is in this case arranged substantially on the axis of the container (the axis is indicated by the reference numeral 20).

Figure 1G:
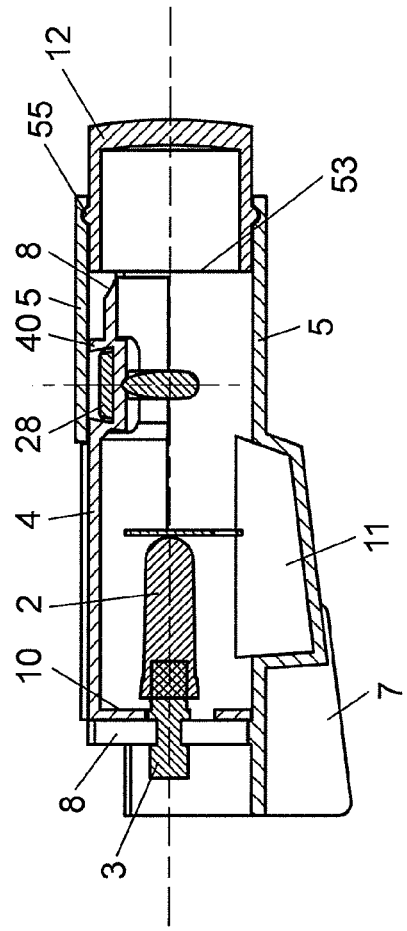
FIG. 1g) shows the section E-E indicated therein, i.e. an axial section in a perpendicular plane.

In FIG. 1, a perspective view of the closed package container with the dental implant arranged therein is shown. As far as the actual implant that is inserted into the human body to remain there is concerned, the dental implant is arranged in a compartment 51 of the package. The mounting holder 3, formed here as a hexagon, protrudes out of this compartment 51, to be precise by a neck 3' that is arranged between the mounting holder 3 and the actual implant 2 being firmly clamped in a housing wall or front terminating plate 8. A slot 9 arranged in this housing wall 8 thereby engages in the narrowed region of the neck 3'.

The package has a front side 21 or a front end and a rear end 22. The actual housing 5 has a substantially closed cylindrical portion in the rear region, and in this cylindrical portion a window is provided toward the front end 21, so that in the front region the housing is formed as an upwardly open segment of a hollow cylinder. The actual housing is correspondingly formed in the front region as a trough, in which the housing wall 8 in the form of a circular disk is fastened perpendicularly in relation to the axis 20. This housing wall 8 forms the separating wall between the open region 19, in which the mounting holder 3 for coupling a tool is exposed, and the actual compartment for the dental implant. This compartment 51 is closed by the cover 4, which is rotatable about the axis 20 and mounted in the housing 5. The cover 4 has an axially running grip 6. The cover extends on the front side up to the housing wall 8 and also has on its front side a sealing region 10, which is likewise formed as a wall region arranged perpendicularly in relation to the axis and is normally formed in one piece with the cover. The sealing region 10 adjoins the front terminating plate 8 as flush as possible and correspondingly seals the compartment 51 in the closed state, as shown in FIG. 1, since without the presence of this additional wall 10, said compartment would have a hole in the region of the slot. Correspondingly, the sealing region 10 additionally has in the region of the implant a semicircular recess, in which the neck 3' comes to lie.

On the rear side, however, the cover 4 extends still further into the cylindrical region of the housing and slides in it. Partly as a result, the guidance of the cover in the interior of the cylindrical housing is ensured. In the case of this exemplary embodiment, however, the healing cap 28 is also arranged in this rear region. The healing cap 28 is fastened to the cover 4.

Arranged right at the rear end 22 of the package 1 is a liquid cartridge 12, which is formed as a cylinder and which has substantially been pushed partially into the interior space of the housing. The liquid cartridge 12 thereby adjoins a release mechanism 18, which in this case is provided as a curved piercing device formed onto the cover and which has the effect when, as shown in FIG. 2, the liquid cartridge is pressed into the cylindrical housing along a pressing-in direction 23 that the liquid cartridge 12 or the membrane 53 thereof is pierced and the liquid component contained in the liquid cartridge can flow into the compartment 51 with the cover 4 closed. The liquid 32 thereby flows into a collecting container 11 formed onto the cylindrical region on the underside of the container and collects in it. The liquid cartridge 12 has on its cylindrical circumference that protrudes into the housing 5 a surrounding, or only intermittently formed, ridge 55, which engages in a corresponding surrounding groove in the inner surface of the cylindrical region of the housing 5 in which the liquid cartridge 12 is arranged. The liquid cartridge 12 is held by this groove/ridge fastening for transportation and before it is pierced open, but the liquid cartridge can nevertheless be easily inserted into the housing during assembly.

The housing 5 also has in the front region two feet 7, which are formed on more or less tangentially to the cylindrical region 14, and, in the sense of extensions of these feet 7 toward the rear region, webs 15. The feet 7 together with the webs 15 have the effect that the package 1 can be readily placed stably on a surface area. Apart from a holder for the healing cap, likewise formed onto the cover 4 is a pattern of slots 25, in which a delimiting strip 24 can be firmly clamped, according to the length of the dental implant 2.

Once the liquid cartridge has been released, as shown in FIG. 2, and the liquid 32 is in the collecting container 11, and consequently in the compartment 51 for the actual implant, the package can be shaken and wetting of the surface of the actual implant 2 with the liquid 32 thereby takes place.

Subsequently, as shown in FIG. 3, the container can be opened by taking up the cover by the grip 6 and swinging it along the arrow 31. The removal opening 30 is thereby exposed and at the same time however the slot 9 in the front terminating plate 8 is also released. Then, as shown in FIG. 4, by taking it up by the mounting holder 3, the implant 2 is released from the widened region 35 of the slot 9 and pushed out upwardly through the narrowed region 36 of the slot 9. To make this easier, the two feet 7 are pressed together, as represented by the arrows 39. This pressing together has the effect that the narrowed region 36 widens on account of the elasticity of the materials used, and the dental implant 2 can be removed upwardly out of the package, substantially without any force being applied. A gripping aid 38 (depression, guiding grooves/webs) may in this case make handling easier.

In connection with FIG. 5, it is also intended moreover to show how a spreading slot 52, which extends downwardly from the gap 9, is preferably arranged in the front terminating plate 8. This spreading slot 52 is normally as good as completely closed and substantially tight; it serves the purpose of making it easier for the front terminating plate 8 to be spread open when pressing is performed according to arrow 39 in FIG. 4.

The container opened in this way can then be left standing without any problem (cf. FIG. 5), since the healing cap is still arranged inside the container and is correspondingly not exposed, and cannot become contaminated, and since furthermore, as can be seen in particular from the section according to FIG. 3b), the cover 4 has moreover also been pushed over the collecting container 11 and the upper access opening 33 thereof, and consequently covers in the upward direction the liquid 32 arranged in the collecting container 11. The liquid 32 is correspondingly not exposed and also cannot be contaminated or escape from the region covered by the cover in the possible event of, for example, such a container being inadvertently tipped over.

Figure 6:
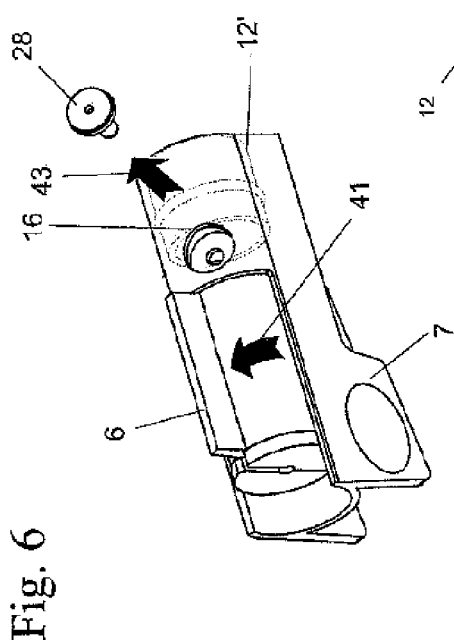
FIG. 6 shows a perspective view of a package according to FIG. 1, partially closed for the removal of the healing cap.
Figure 7:
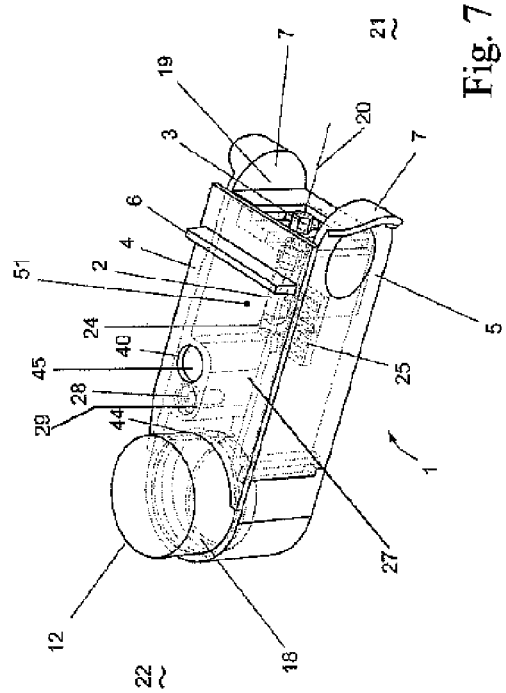
FIG. 7 shows a perspective view of a closed package according to a second exemplary embodiment.

As shown in particular in FIG. 3, an opening 16 for the healing cap 28 is provided in the cylindrical region of the housing. The actual healing cap 28 is fastened in the cover 4, to be precise by means of a holder 29. The healing cap 28 can only be made accessible, however, when the cover 4 is turned back into a middle position along arrow 41, as shown in FIG. 6, so that the opening 16 in the housing is brought into line with a removal opening 40 provided in the cover. Then the healing cap 28 can be taken up from the outside by means of a corresponding tool and, as represented by the arrow 43, removed from the package. As a result, the healing cap 28 is always arranged such that it is inside the package, and completely protected, both when the package is closed (cf. FIG. 1) and when the package is opened (cf. for example FIG. 5) and a specific separate step is required to expose the healing cap. This is a major advantage, for example over the known packages for such dental implants, in the case of which the healing cap is normally also exposed at the same time when a cover is opened, which is problematic if the package is not carefully handled.

In this exemplary embodiment, the healing cap 28 is arranged more or less in a blind hole on the cover 4. Correspondingly, the healing cap is also not contacted or wetted by the liquid 32. This is normally the preferred variant, since the healing cap does not of course generally come into contact with the human tissue (it normally serves the purpose of closing the blind hole in the implant for a limited period of time until the actual crown is fitted), and since the healing cap is also not intended to grow in. In particular whenever, as normally preferred, the liquid exhibits a healing-promoting effect, it would even be of disadvantage if the healing cap were wetted by this healing-promoting liquid. It is, however, also quite possible to arrange the healing cap in the container in such a way that it is likewise wetted by the liquid during shaking; this may, for example, be of advantage whenever the liquid serves, for example, exclusively for preventing inflammation, which may also be desired for the healing cap 28. Thus, for example, in the case of the third exemplary embodiment (compare further below), the healing cap is let in in such a way that its lower part, which is later inserted into the implant, can be wetted by the liquid. By contrast, the upper part of the healing cap, on the other hand, which could come into contact with human tissue after the implantation, is substantially not wetted. Such a type of construction has the advantage that the package can be given a more simple design, since no region that is sealed off with respect to the liquid has to be provided in the cover for the lower part.

A further exemplary embodiment of a package is shown in FIGS. 7 to 12. The package 1 is in this case formed as an elongated box 5, in the case of which the open region 19 is likewise arranged between two feet 7 at the front end 21, at the place where the mounting holder 3 protrudes from the compartment 51.

At the rear end 22 is the liquid cartridge 12; here, too, the liquid cartridge 12 is of a cylindrical form, but here is fitted onto the box-shaped package more or less from above and protrudes beyond it. Correspondingly, the box-shaped package is also designed such that it is rounded off at the rear end 22. The release mechanism 18 is located underneath the liquid cartridge 12.

The housing 5 has a bottom and two side walls, and arranged on the bottom is a pattern of slots 25, in which in turn a delimiting strip 24 can be firmly clamped in a way corresponding to the dimensioning of the implant. On the upper side, the housing 5 has an opening, which is closed by the cover 4, which completely closes off this opening. The cover 4 has at its front end a grip 6 and is of a transparent form. The cover consequently closes the compartment 51 in the upward direction. The cover has a removal opening 40 for a healing cap.

In this case, however, the healing cap 28 is not fastened on or in the cover, as in the case of the previous exemplary embodiment, but instead there is in the compartment a region that is referred to here as the closure region 27 and in which the healing cap 28 is fastened in a holder 29. When the container is closed, the removal opening 40 is in line with the region 45, and the compartment 51 is correspondingly closed in a liquid-tight manner in spite of the presence of the removal opening 40. Also in the case of this exemplary embodiment, although the healing cap is arranged in the compartment 51, if liquid is present in the compartment 51 it does not come into contact with the healing cap since the latter is captured in the covering 45 in a blind-hole-like recess closed by the cover 4.

As shown in FIG. 8, here the liquid cartridge 12 can be pressed into the package by pressing-in along the arrow 23, and the liquid stored in the cartridge is thereby released from it and flows into the compartment 51. As already in connection with the first exemplary embodiment, it should be pointed out that the cartridge can also be released by a turning movement or by a combined movement involving both turning and pressing downward (for example by an internal thread being formed in the housing in that region where the cartridge is arranged and by the cartridge having a corresponding external thread). Once the cartridge has then been released, the implant can be wetted or coated with the liquid located in the compartment 51 by shaking.

It is shown in FIG. 9 how the package can be opened by displacing the cover 4 rearwardly in a direction 31. The cover 4 has at its rear end a round recess 44. In the closed state (cf. FIG. 7), this recess 44 adjoins the circumferential surface of the liquid cartridge. If, as shown in FIG. 9, the liquid cartridge 12 is then pressed completely into the container, the recess 44 is exposed and the cover 4 can correspondingly also only be pushed rearwardly when the liquid cartridge 12 is either completely pressed in (12') or else has been removed in advance. Furthermore, on the box form, which is of a double-walled design on one side, latching recesses 54 can be seen in the gap between the two walls. The guiding web 49, described in detail further below, has a corresponding latching detent, which is arranged at the same level and inwardly directed and which defines by its engagement in the latching recesses 54 the closed position of the cover (latching recess on the right) as well as the position for removal of the healing cap (compare FIG. 12, latching recess on the left).

The then exposed implant 2 can then be removed from the compartment 51 by being held by the mounting holder 3. This is specifically shown in FIG. 10.

Here it is also shown how this removal is only possible when the two feet 7 are pressed together along the pressing direction 39. In fact, the exemplary embodiment has a special holding mechanism for the implant, which is to be explained in detail in connection with FIG. 11. The housing is in this case of a two-part design; there is a first housing part 46 and a second housing part 47; although these two housing parts are formed or connected to each other in one piece, they are displaceable in relation to each other in the front region 21. Namely, the first housing part forms a substantially rigid unit with the foot 7 represented on the left side in FIG. 11 and on the other hand forms the side area arranged on the right side of the gap 9 or of the regions 35 and 36. Equally, this first housing part 46 forms the outer, rearwardly extending side wall.

The second housing part 47 for its part forms on the one hand the right, rearwardly extending side wall, structurally is rigidly connected to the right-hand foot but also forms, moreover, the left-hand delimiting area of the gap 9 as well as a second, rearwardly extending side wall, arranged inside on the left side. On account of the flexibility (bending flexibility) of the materials used, in the case of this structural design the two housing parts 46 and 47 are mounted displaceably in relation to each other (a seal 48 may optionally be arranged in order to ensure the liquid tightness), and, since the two parts form different sides of the gap 9 which lie opposite the respectively rigidly coupled-on foot 7, the two parts can be displaced toward each other by pressing the two feet 7, and the gap 9 thereby opens, so that the narrowed region 36 widens and the implant can be removed in the upward direction. It is thus possible to hold the implant really firmly in the widened region 35 and to design the region 36 in such a way that it is closed in a liquid-tight manner, preferably without further sealing means, as long as the two feet 7 are not pressed together.

Both the first housing part 46 and the second housing part 47 form a lateral wall portion arranged on the same side of the housing. These two wall portions are spaced apart by a gap 50. The cover then has at its end facing the front end 21 a downwardly directed guiding web 49, which engages at least partially in this gap 50 and has approximately a thickness that corresponds to the width of this gap 50. If the cover is then in the front position, the guiding web 49 lies in the gap 50 and prevents the possibility of the latter being pressed together, and consequently also prevents the possibility of the gap 9 being opened and the implant removed. Only when the cover has been pushed rearwardly and the guiding web 49 has been displaced rearwardly in the gap 50 can the gap 50 be pressed together, by pressing together the feet 7 in the front region, and consequently can the gap 9 also be opened and the implant thereby released.

Figure 12:
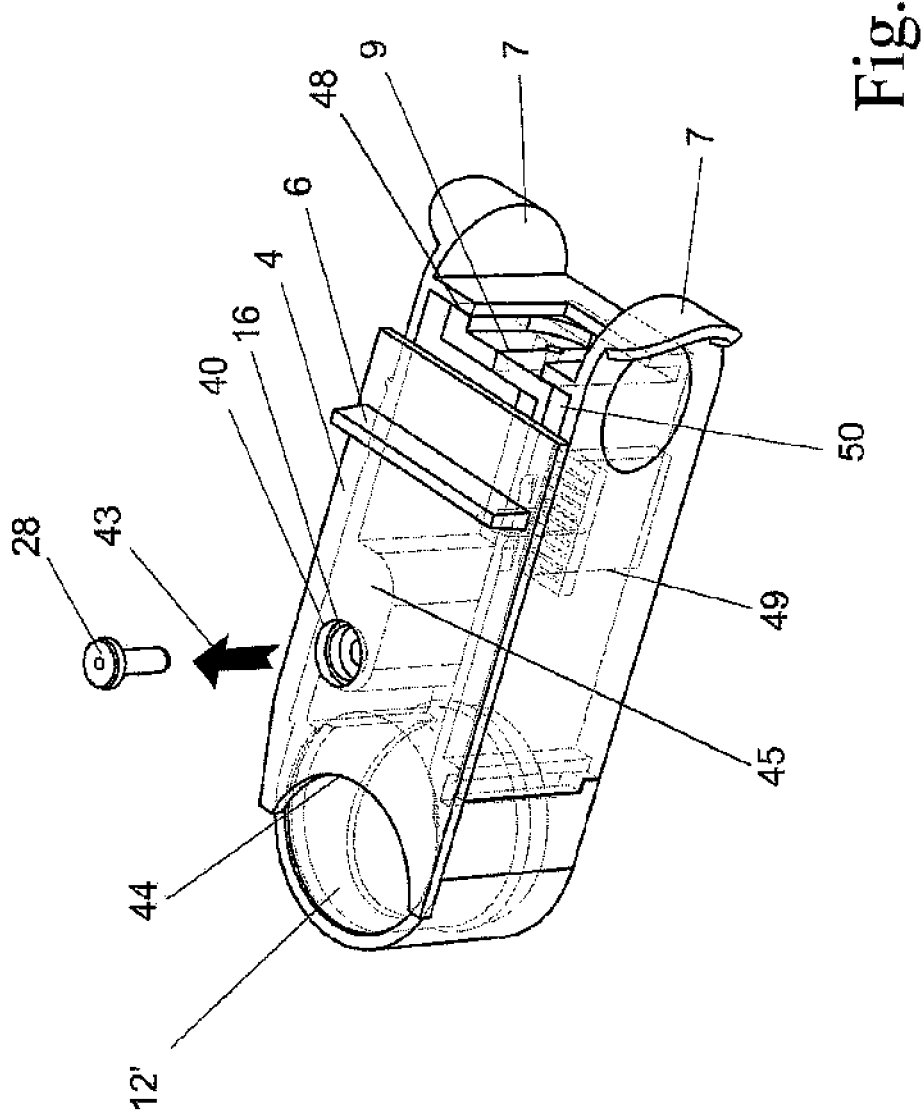
FIG. 12 shows a perspective view of a package according to FIG. 7, partially closed for the removal of the healing cap.
Figure 13F:
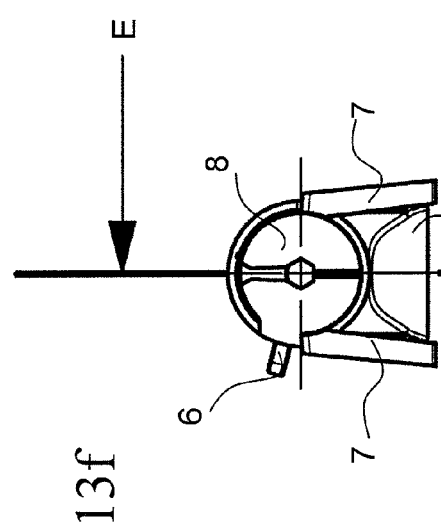
FIG. 13f) shows a frontal view.
Figure 13G:
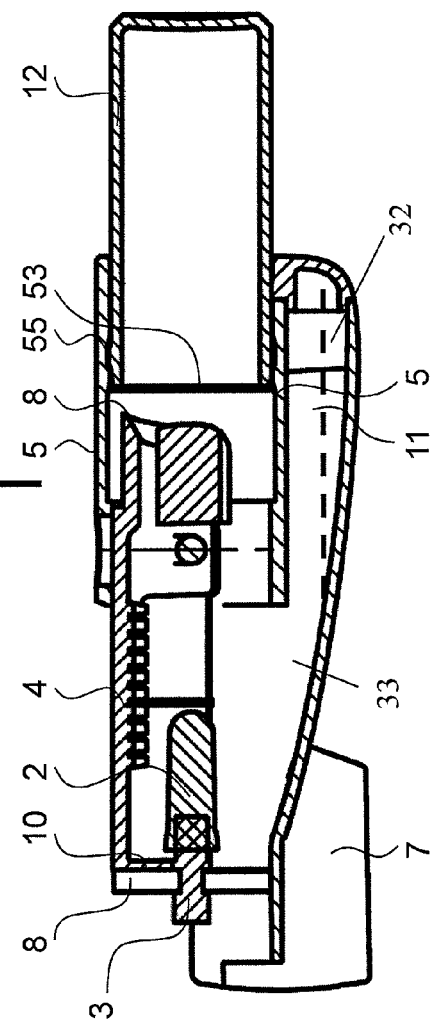
FIG. 13g) shows the section E-E indicated therein, i.e. an axial section in a perpendicular plane.
Figure 17:
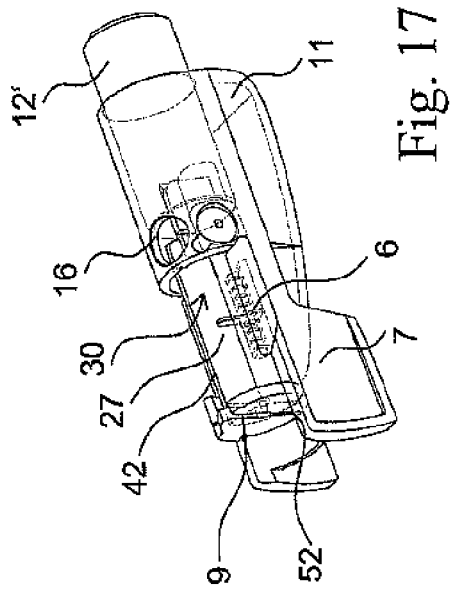
FIG. 17 shows a perspective view of an opened and empty package according to FIG. 13.
Figure 16:
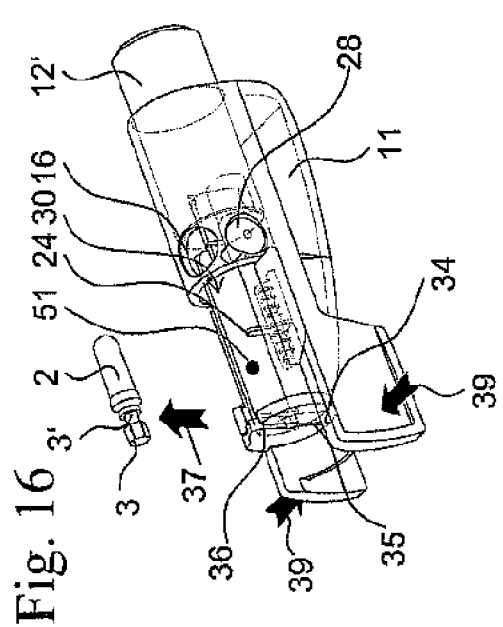
FIG. 16 shows a perspective view of an opened package according to FIG. 13, in which the implant is removed.
Figure 18:
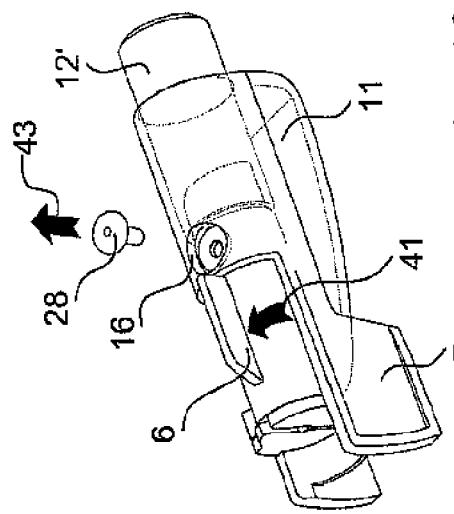
FIG. 18 shows a perspective view of a package according to FIG. 13, partially closed for the removal of the healing cap.

FIG. 12 shows the container after the cover 4 has been pushed from the rearmost position, as shown in FIG. 10, forward again to some extent (there is preferably an intermediate latching position here), the removal opening 40 having been brought into line with an opening 16 for the healing cap in the covering 45. In a corresponding way, the healing cap 28, as represented by the part 43, can then be removed from the package, for example by a tool engaging in the blind hole arranged in the top of the healing cap.

FIGS. 13-18 show a third exemplary embodiment, which is similar to the first exemplary embodiment. The same reference numerals designate equivalent elements in the case of this third exemplary embodiment as those already used and described in the case of the first exemplary embodiment. The individual functions of individual elements and the method steps of the manipulation are correspondingly analogous to those in FIGS. 1-6 and are not to be repeated again.

This third exemplary embodiment differs, however, particularly from the first exemplary embodiment, in that the collecting container 11 for the liquid has been displaced somewhat more to the rear side of the pack, that is to say is no longer completely arranged only under the compartment 51. As a result, the collecting container 11 is displaced more or less under that region into which the liquid cartridge 12 is also pushed. As can be seen in particular from FIG. 13g, the collecting container 11 is thus displaced substantially with its main volume under the housing portion 5, which surrounds the cartridge. Thus, when it is no longer used and is lying in the collecting container, the liquid is not only retained in this collecting container 11 by the cover 4, as long as the latter is in the open state, but is in principle removed further from the space 51 and covered by the region of the cartridge, and thus also hindered to a greater extent from escaping. Furthermore, the bottom of the collecting container 11 is sloping downwardly toward the rear end of the package, that is to say that end where the liquid cartridge is arranged. The liquid flowing away from the compartment 51 into the collecting container 11 is thus removed to the rear region of the collecting container 11 and mainly collected in that region. Moreover, the collecting container 11 provides a standing area on the rear side, which dispenses with the need for the webs 15.

A further difference from the first exemplary embodiment can be seen in the design of the release element 18. This is in this case formed as a cutting edge made to extend approximately in a quarter circle, wherein the edge is inclined with respect to the plane of the sealing membrane 53. This has the effect that this cutting edge forms a point 57, which faces the membrane 53 and comes into contact with the membrane at the first moment the cartridge 12 is inserted, so that the cutting edge 18 successively continues to cut open the membrane 53 in a circular motion as the cartridge continues to be pushed in. In this way, the resistance during the pushing-in of the cartridge 12 is reduced and the precision during the cutting-open is increased.

In the case of this exemplary embodiment, the release element 18 also has a pushing-away web 56'. This is arranged more or less centrally within the cutting edge and is preferably formed on it in one piece, and has the effect that, when the cartridge 12 has been pushed in and the cutting edge has cut into the membrane, the central region of the membrane is also actually flipped out from the opening in the cartridge 12 inwardly into the cartridge 12. The front edge of this web 56 that is facing the membrane 53 preferably lies approximately at the axial level of the rearmost portion of the inclined cutting edge 18. As a result of the not inconsiderable surface tension and the quite stiff materials that are often used for the membrane (the membrane often comprises a metal foil, for example an aluminum foil, as one of the layers), without such a measure with an element 56 it is often difficult to make the liquid leave the cartridge 12 into the compartment 51 at all with a narrow cut edge made by the cutting edge if the membrane is not actively pushed or flipped out of the way.

LIST OF DESIGNATIONS 1 package
2 dental implant with mounting holder
2' dental implant
3 mounting holder of 2
3' neck on 3, transitional portion
4 cover
5 housing
6 grip on 4
7 feet on 5
8 front terminating plate, housing wall
9 slot in 8
10 sealing wall portion, sealing region on cover for terminating plate
11 collecting container for liquid
12 liquid cartridge (unopened)
12' liquid cartridge (opened)
13 overhang of 12
14 region of 5 in the form of a segment of a hollow cylinder
15 webs on 5
16 opening in 5 for healing cap
17 sealing region on cover for 16
18 release element for 12
19 open region of 1
20 axis
21 front end of 1
22 rear end of 1
23 pushing-in direction for liquid cartridge
24 delimiting strip
25 pattern of slots for 24
26 closure overhang on 4
27 closure region of 4
28 healing cap
29 holder for 28 on 4
30 removal opening
31 turning direction/pushing direction for opening of 4
32 liquid from liquid cartridge
33 upper access opening for 11
34 stop edge
35 widened region of 9
36 narrowed region of 9
37 direction of removal for 2
38 gripping aid on 7
39 pressing direction for removal of 2
40 removal opening for 28 in 4
41 turning direction for closure of 4
42 rear edge of 4
43 direction of removal for 28
44 recess in 4 for 12
45 covering
46 first housing part
47 second housing part
48 seal
49 guiding web
50 gap between 46 and 47
51 compartment for implant
52 spreading slot
53 sealing membrane on 12
54 latching recesses for latching projections on 49
55 ridge on 12
56 pushing-away web
57 point of 18

The invention claimed is:

1. A package for a dental implant, said dental implant comprising a first solid portion structured for insertion into a human body or human bone or tissue and a second solid portion in the form of a mounting holder,
said package comprising:
a housing, which has a compartment for said first solid portion, which compartment comprises a pivotable or slidable cover and which compartment can be closed by said cover so as to be substantially liquid-tight and
a region for a front part of said mounting holder, which region is separated from said compartment by a housing wall,
wherein a passage connecting said compartment and said region is present in said housing wall for a rear part of said mounting holder,
wherein said housing wall has a removal slot, which allows the implant to be removed when said cover is open, without separating said first portion from said mounting holder,
wherein the package has at least one liquid cartridge and an associated release element, and
wherein, with said cover closed, the liquid cartridge can be opened by means of said release element in such a way that liquid located in the liquid cartridge can flow out into the compartment to wet a surface of said first portion.

2. The package as claimed in claim 1, wherein the housing is formed in an elongated manner with a front end and a rear end, and wherein the region for the second portion of the implant is arranged at the front end, the liquid cartridge is arranged at the rear end, and the compartment is arranged in between.

3. The package as claimed in claim 1, wherein, with the cover closed, the region is freely accessible, and is intended for a mounting holder for the implant.

4. The package as claimed in claim 1,
wherein the package is structured to receive a healing cap, and said cover has an opening for the removal of the healing cap and the housing has a healing cap opening for the removal of said healing cap, and
wherein, with said healing cap arranged in the housing, the healing cap opening is covered by the cover both when the cover is completely closed and when the cover is completely open, but
wherein the healing cap opening of the housing is only exposed in the case of an intermediate position of said cover, in which intermediate position the opening of said cover is brought in line with the healing cap opening.

5. The package as claimed in claim 1, wherein the compartment has in the region a collecting portion for the liquid of the liquid cartridge, which collecting portion has a void volume which is smaller than or corresponds substantially to a liquid volume of the liquid cartridge, and wherein said collecting portion is closed or at least covered by the cover when the package is completely open.

6. The package as claimed claim 1,
wherein the housing has a wall region in the form of a segment of a hollow cylinder, which together with a cover wall region that is likewise in the form of a segment of a hollow cylinder and arranged coaxially in relation to the wall region in the form of a segment of a hollow cylinder of the housing, substantially delimits the compartment,
wherein said region is separated from said compartment by a housing wall arranged perpendicularly in relation to an axis and in the form of a circular disk or in the form of a segment of a circle, wherein said housing wall has a passage that is arranged substantially on said axis and is upwardly open by means of a narrowed slot,
wherein said cover is mounted rotatably about said axis,
wherein said cover slides substantially flush on an inner side of the housing, with its outer surface, and can be pivoted from a closed state into an open state, and
wherein the cover has on an axial periphery, facing the housing wall, a sealing wall portion passing over the same angular range as the cylinder segment of the cover and arranged perpendicularly in relation to the axis.

7. The package as claimed in claim 6, wherein the wall region of the elongated housing in the form of a segment of a hollow cylinder protrudes in the axial direction toward a front end beyond the housing wall, at least as far as the second portion of the implant, or somewhat further than the second portion, such that the region is open in axial and upward directions, and
wherein, at an opposite rear end, the housing has a substantially closed region in the form of a hollow cylinder in which there is arranged a liquid cartridge, which is of a substantially cylindrical form and coaxially arranged and can be pushed in the axial direction into this region, wherein, furthermore, the release element optionally initiates the release of the liquid when the liquid cartridge is pushed into the housing in the axial direction as far as a stop.

8. The package as claimed in claim 6, wherein the wall region of the housing in the form of a segment of a hollow cylinder covers an angular range around the axis of 120-210°, or wherein the portion of the cover in the form of a segment of a hollow cylinder covers an angular range of 120-270°.

9. The package as claimed in claim 6, wherein the housing has, at least at its front end, two lateral, downwardly protruding feet, arranged tangentially and substantially parallel to each other or widening downwardly, and webs adjoining thereto and extending toward the rear end, wherein the housing wall is joined on in such a way that pressing together of the two feet brings about a widening of the narrowed slot that facilitates the removal of the implant.

10. The package as claimed in claim 1, wherein the housing is substantially formed as an elongated, upwardly open box, wherein the region is arranged at a front end and the liquid cartridge is arranged at an opposite rear end, the liquid cartridge being of a cylindrical form with its axis perpendicular to the longitudinal direction of the housing and arranged such that it protrudes at least partially upward out of the latter, wherein the cover closes this upper opening and can be displaced along the longitudinal direction of the housing toward the rear end, exposing the upper opening, wherein this opening displacement of the cover is only possible if the liquid cartridge has either been removed from the housing or has been pressed into the housing, thereby releasing the liquid.

11. The package as claimed in claim 10, wherein the housing wall is formed by a first housing part and a second housing part, wherein the slot or the widened region and the narrowed or even closed region are delimited on one side by the first housing part and on the other side by the second housing part, and wherein the first housing part can be displaced in relation to the second housing part substantially in a direction perpendicular to the longitudinal axis of the housing, thereby widening or opening the region.

12. The package as claimed in claim 11, wherein each of the first housing part and the second housing part forms at least one lateral wall portion arranged on a same side of the housing, and
wherein said wall portions are spaced apart by a gap, and
wherein the cover has at an end facing a front end a guiding web, which engages at least partially in said gap.

13. The package as claimed in claim 1, wherein the cover or at least regions of the housing are transparent or translucent, so that an implant arranged in the package and/or a healing cap arranged in or on the package can be identified.

14. The package as claimed in claim 1 with a dental implant arranged in it, wherein a liquid with which the surface of the dental implant is wetted or rinsed shortly before its insertion into the human body is arranged in the liquid cartridge, wherein this liquid is an aqueous solution of a component exhibiting at least one of the following effects: promoting healing, preventing inflammation or infections, promoting bone growth, promoting tissue growth, preventing bone degradation, stabilizing or improving the bone density in the surroundings of the implant, improving the bone-implant contact by increasing the amount of bone or soft tissue growing on the implant.

15. The package as claimed in claim 1,
wherein the package is intended for additionally receiving a healing cap in that the healing cap is arranged in or on the cover, and said cover has an opening for the healing cap and the housing has a healing cap opening for the removal of said healing cap, and
wherein, the opening in said cover is covered by the housing both when the cover is completely closed and when the cover is completely open and is only exposed in the case of an intermediate position of the cover by bringing the opening of the cover into line with the healing cap opening.

* * * * *